(12) United States Patent
Hori et al.

(10) Patent No.: US 7,790,702 B2
(45) Date of Patent: Sep. 7, 2010

(54) LIPID METABOLISM IMPROVING AGENT

(75) Inventors: Goro Hori, Tsuchiura (JP); Kazuhiro Matsuoka, Komae (JP); Iwao Sato, Tsuchiura (JP); Satoshi Nagaoka, Gifu (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 894 days.

(21) Appl. No.: 11/368,645

(22) Filed: Mar. 7, 2006

(65) Prior Publication Data

US 2006/0160725 A1 Jul. 20, 2006

Related U.S. Application Data

(63) Continuation of application No. 09/544,632, filed on Apr. 6, 2000, now abandoned, which is a continuation of application No. 09/106,004, filed on Jun. 29, 1998, now abandoned, which is a continuation of application No. 08/836,546, filed as application No. PCT/JP96/02549 on Sep. 6, 1996, now abandoned.

(30) Foreign Application Priority Data

Sep. 6, 1995 (JP) .................................. 95/228928

(51) Int. Cl.
A61K 31/685 (2006.01)
(52) U.S. Cl. .......................................... 514/78; 514/75
(58) Field of Classification Search .................. 514/78, 514/75
See application file for complete search history.

(56) References Cited

U.S. PATENT DOCUMENTS

| 5,079,028 A | 1/1992 | Wieske et al. |
| 5,109,118 A | 4/1992 | Mizushima |
| 5,310,958 A | 5/1994 | Mizushima |
| 5,362,491 A | 11/1994 | Mizushima |
| 5,578,639 A * | 11/1996 | Homan ........................ 514/522 |
| 5,626,873 A | 5/1997 | Weiner et al. |
| 5,650,190 A | 7/1997 | Buikstra et al. |
| 5,785,984 A | 7/1998 | Kurihara et al. |

FOREIGN PATENT DOCUMENTS

| JP | 61-152632 | 7/1986 |
| JP | 63-283735 | 11/1988 |
| JP | 64-52708 | 2/1989 |
| JP | 03-163100 | 7/1991 |
| JP | 06-054650 | 1/1994 |
| JP | 7-48992 | 5/1995 |
| JP | 03-297364 | 7/2002 |
| WO | WO 00/43036 | 7/2000 |

OTHER PUBLICATIONS

J.C., Segen, Ed., *The Dictionary of Modern Medicine*,. Parthenon Publishing Gr., pp. 280 and 394,1994.
Sugano, *J. Nutrit.*, 120, pp. 977, 1990.
Sugano, *Atherosclerosis*, 72, p. 115-122, 1988.
Williams, *Perspectives in Biol. Med.*, 27, p. 417, 1984.
A. Sirtori, *Nutr. Metab.*, 29, p. 348, 1985.
Nagaoka, *Agric. Biol. Chem.*, 3, p. 813, 1991.
C. R. Sirtori, et al., "Cholesterol-Lowering and HDL-Raising Properties of Lecithinated Soy Proteins in Type II Hyperlipidiemic Patents", *Annals of Nutrition and Metabolism*, vol. 29, No. 6, pp. 348-357, 1985.
M. Y. Jenkins, et al., "Effects of Dietary Protein and Lecithin on plasma and liver Lipids and Plasma Lipoproteins in Rats", *Nutrition Reports International*, vol. 28, No. 3, pp. 621-634, 1983.
"Harper's Biochemistry", 25th Edition, pl. 291, Aug. 1999.

* cited by examiner

*Primary Examiner*—Gollamudi S Kishore
(74) *Attorney, Agent, or Firm*—Antonelli, Terry, Stout & Kraus, LLP.

(57) ABSTRACT

The present invention relates to a protein/phospholipid or protein hydrolyzate/phospholipid complex containing 10 wt % or more of bound phospholipid, a lipid metabolism improving agent comprising the complex, and a functional food comprising the complex.

The present invention provides a lipid metabolism improving agent and a functional food, containing the complex.

9 Claims, No Drawings

LIPID METABOLISM IMPROVING AGENT

CROSS-REFERENCE TO RELATED APPLICATION

This application is a Continuation application of application Ser. No. 09/544,632, filed Apr. 6, 2000 now abandoned, which is a Continuation application of application Ser. No. 09/106,004 now abandoned, filed Jun. 29, 1998, which is a Continuation application of application Ser. No. 08/836,546, filed May 6, 1997 now abandoned, the contents of which are incorporated herein by reference in their entirety. No. 08/836,546 is a National Stage Application, filed under 35 USC 371, of International (PCT) Application No. PCT/JP96/02549, filed Sep. 6, 1996.

BACKGROUND ART

The term lipid metabolism refers to the in vivo process of catabolism (decomposition) and anabolism (accumulation) of lipids, which are mainly triglycerides derived from food, and is intended to include, in the broad sense, reactions for transforming lipids into energy, biosynthesis of fatty acids, biosynthesis of acylglycerol. phospholipid metabolism, and cholesterol metabolism [Akira Misaki, Biochemistry for Nutrition, Asakura Shoten (1993), p. 123-134].

In recent years, mortality from adult diseases, particularly cardiovascular disorders, is rapidly rising, and a correlation between occurrence of such disorders and cholesterol concentration in blood has been pointed out. Some attempts have so far been made to lower the cholesterol concentration in blood by the use of specific food components. For example, the following proteins are known as proteins which lower the cholesterol concentration in blood: whey protein [Agric. Biol. Chem., 55, 813 (1991)]; soybean protein [Atherosclerosis, 72, 115 (1988)]; milk serum protein (Japanese Published Unexamined Patent Application No. 176713/93); and soybean protein hydrolyzate [J. Nutr., 120, 977 (1990)].

It is also known that egg yolk phospholipid lowers the cholesterol concentration in blood [Agric. Biol. Chem., 53, 2469 (1989)].

An attempt has been made to lower the cholesterol concentration in blood by the use of a combination of lactalbumin, collagen, soybean protein, or wheat gluten, and soybean lecithin (0, 2.5 and 5%) [*Nutr. Rep. Int.*, 28, 621 (1983)].

Also known is a method for lowering the cholesterol concentration in blood by the use of a textured soybean protein containing 6% of soybean lecithin [*Ann. Nutr. Metab.*, 29, 348 (1985)].

DISCLOSURE OF THE INVENTION

The present invention relates to a protein/phospholipid or protein hydrolyzate/phospholipid complex containing 10 wt % or more of bound phospholipid, a lipid metabolism improving agent comprising the complex, and a functional food comprising the complex.

The proteins for use in the present invention may be derived from animals, plants or microorganisms. Suitable examples are wheat protein, soybean protein, corn protein and milk protein, among which wheat protein and soybean protein are preferred. As the wheat protein, wheat gluten is usually used. Wheat gluten, soybean protein, etc. of commercial origin are readily available.

Examples of the phospholipids are phosphatidyl choline, phosphatidyl ethanolamine, phosphatidyl inositol, phosphatidyl serine, sphingomyelin, phosphatidic acid, and lecithin, which is a mixture of the above members.

Lecithin derived from animals, plants or microorganisms may be used. Suitable examples are brain lecithin, liver lecithin, egg yolk lecithin, soybean lecithin and yeast lecithin, among which soybean lecithin and egg yolk lecithin are preferred.

Lecithin may be used as such, but enzyme-modified lecithin obtained by treating lecithin with an enzyme such as phospholipase is preferably used. Lecithin and enzyme-modified lecithin of commercial origin are readily available.

The term bound phospholipid as used herein refers to a phospholipid which remains bound to a protein after being treated with a nonpolar organic solvent such as petroleum ether.

The amount of bound phospholipid is calculated as follows. The amount of total phospholipid contained in a protein hydrolyzate/phospholipid complex is determined. Then, the complex is treated with a nonpolar organic solvent such as petroleum ether, and the amount of phospholipid extracted into the solvent (hereinafter referred to as free phospholipid) is determined. The amount of bound phospholipid is calculated as the difference between the amount of total phospholipid and that of free phospholipid.

The bound phospholipid content of a complex is calculated as the percentage of bound phospholipid in the complex (wt %).

The complex of the present invention contains 10% or more, preferably 10-50% of bound phospholipid. Particularly preferred is the complex containing 20-50% of bound phospholipid.

As the protein/phospholipid complex, commercially available ones can be used. The protein/phospholipid complex can also be prepared by mixing 100 parts by weight of a protein and 10-100 parts by weight of a phospholipid using a stirring mixer, preferably in the presence of water. By mixing a protein and a phospholipid at a ratio of 100:20-50 by weight, preferably 100:30-40, a desirable complex can be obtained wherein the bound phospholipid content is high and the ratio of bound phospholipid to total phospholipid is high. In an exemplary preparation process, a solution prepared by dispersing a phospholipid in water is added to a protein, followed by mixing at room temperature by using a high power mixer (50-200 r.p.m.) or a homogenizer (5,000-15,000 r.p.m.).

The protein hydrolyzate/phospholipid complex can be prepared by mixing a protein hydrolyzate and a phospholipid, or by hydrolyzing in an aqueous medium the protein moiety of a complex prepared by mixing a protein and a phospholipid.

As the protein hydrolyzate, hydrolysed products of proteins in an aqueous medium using a proteolytic enzyme or an acid can be used. Preferred are hydrolyzates slightly soluble in water having a molecular weight of 5,000-30,000, particularly, those having a molecular weight of 10,000-20,000.

A typical example of the method for preparing such slightly water-soluble substances is given below. A protein is dispersed in water, and hydrochloric acid or sodium hydroxide is added to the solution to bring it to the optimum pH range for the proteolytic enzyme to be employed. The proteolytic enzyme is added to the solution in an amount of 0.5-2% based on the substrate protein, followed by reaction at the optimum pH and the optimum temperature for the enzyme for 20-30 hours. The enzyme reaction is terminated by heating at 85-95° C. for about one hour. After being neutralized with sodium hydroxide or hydrochloric acid, the reaction mixture is centrifuged to obtain the slightly water-soluble substance.

As the aqueous medium, water, buffers, alcohols, esters, ketones, amides, etc. can be used. Water is preferably used.

As the proteolytic enzyme, pepsin, trypsin, pancreatin, papain, etc. can be used.

The protein hydrolyzate/phospholipid complex can be prepared by mixing 100 parts by weight of a protein hydrolyzate and 10-100 parts by weight of a phospholipid using a stirring mixer, preferably in the presence of water. By mixing a protein and a phospholipid at a ratio of 100:20-50 by weight, preferably 100:30-40, a desirable complex can be obtained wherein the bound phospholipid content is high and the ratio of bound phospholipid to total phospholipid is high. In an exemplary preparation process, a solution prepared by dispersing a phospholipid in water is added to a protein hydrolyzate, followed by mixing at room temperature by using a high power mixer (50-200 r.p.m.) or a homogenizer (5,000-15,000 r.p.m.).

The protein hydrolyzate/phospholipid complex can also be prepared by the same method as in the preparation of a protein hydrolyzate except that a protein/phospholipid complex is used instead of a protein hydrolyzate. By this method, the protein moiety of the complex is hydrolyzed to give the desired complex as a slightly water-soluble substance having a molecular weight of 5,000-30,000, preferably, 10,000-20,000. The hydrolysis of the protein moiety of the complex is preferably carried out by the treatment with a proteolytic enzyme in an aqueous medium.

As the method for the preparation of the protein hydrolyzate/phospholipid complex, the hydrolysis of the protein moiety of a protein/phospholipid complex in an aqueous medium is preferable to the mixing of a protein hydrolyzate and a phospholipid, because the former gives a higher protein recovery.

The complex of the present invention may be utilized without being isolated from the reaction mixture, or after isolation and purification from the reaction mixture. The product obtained by drying the reaction mixture or the complex by freeze-drying or spray-drying and pulverizing the dried product can also be utilized.

The protein hydrolyzate/phospholipid complex is superior to the protein hydrolyzate/phospholipid complex in lipid metabolism improving effect.

The lipid metabolism improving agent of the present invention may be in any of the dose forms such as tablets, powders, fine granules, granules, capsules, syrups, enteric coated tablets, troches, and liquid preparations for oral administration.

The administration route for the lipid metabolism improving agent of the present invention is not specifically limited, but oral administration is preferred. In the case of oral administration, the complex of the present invention may be administered as it is, or in the form of compositions prepared by conventional methods using excipients which are acceptable as ingredients of food or drugs.

As the excipients, saccharides such as sorbitol, lactose and glucose, inorganic substances such as dextrin, starch, calcium carbonate and calcium sulfate, crystalline cellulose, distilled water, sesame oil, corn oil, olive oil, cottonseed oil, and other generally employed excipients can be used.

In preparing the compositions, additives such as binders, lubricants, dispersing agents, suspending agents, emulsifiers, diluents, buffers, antioxidants, and antibacterial agents may be used.

The dose of the composition will vary depending on various factors such as the patient's age, sex and physical condition, administration route, administration schedule, and form of composition. For instance, when the composition is orally administered to an adult, it is suitable to administer the composition in an amount of 2-100 g/day in 1 to 4 parts. Administration may be made at a dose outside the above limit as may be required.

The lipid metabolism improving agent of the present invention can be used not only as a cholesterol metabolism improving agent but also as an agent for the treatment or prevention of diseases such as fatty liver, hypertension, hyperlipidemia, arteriosclerosis, obesity, diabetes, and myocardial infarction.

The functional food of the present invention can be produced by adding the protein hydrolyzate/phospholipid complex containing 10% or more of bound phospholipid to food materials in a conventional process for producing food. The functional food contains 0.1% or more, preferably 0.1-50%, more preferably 0.5-30% of the complex. The functional food may additionally be formulated to contain a protein, a sugar, a fat, a trace element, a vitamin, an emulsifier, a flavor, and the like.

The term functional food as used herein refers to food designed and processed so that food ingredients may fully perform their functions for the biophylaxis, regulation of biorhythm, and regulation of physical condition relating to the prevention of and recovery from diseases.

Examples of the food are juice, soft drinks, tea, lactic acid beverages, ices, milk, dairy products (e.g. butter, cheese, yogurt, processed milk, and skim milk), meat, meat products (e.g. ham, sausage, and hamburger), fish, fish products (e.g. steamed, baked or fried fish paste), egg, egg products (e.g. fried or steamed foods made of beaten eggs), confectionery (e.g. cookies, jelly, and snacks), bread, noodles, pickles, smoked fish and meat, dried fish, preserved foods boiled down with soy, salted foods, soup, and seasonings.

The functional food of the present invention may be in the form of ordinary food, or in the form of liquid food, pre-digested nutrient food, elemental diet, liquid nutrient food, or the like.

The functional food of the present invention can be used not only for improving lipid metabolism, particularly cholesterol metabolism, but also for treating, preventing or alleviating diseases such as fatty liver, hypertension, hyperlipidemia, arteriosclerosis, obesity, diabetes, and myocardial infarction. It is suitable to give the functional food to an adult in an amount of 2-100 g/day.

The effect of the complexes of the present invention is shown below by Test Examples.

TEST EXAMPLE 1

Test Method

Five-weeks-old male Wistar rats were used as test animals. The rats were fed with a commercially available solid feed (MF, Oriental Yeast Co., Ltd.) for three days, and then divided into groups each consisting of 6 animals in such a way that there is no significant difference in body weight of the animals between the groups. The test feed compositions were formulated, as shown in Table 1, to respectively contain a protein at a protein level of 20% and to contain sucrose in amounts adjusted so as to make the total weights of all the compositions equal. After groups of test animals were fed with equal amounts of the respective feed compositions for 10 days, the total cholesterol concentration in serum, the high density lipoprotein (HDL) cholesterol concentration in serum, and the total cholesterol concentration in liver were measured for each rat.

TABLE 1

| Ingredient | Test Group 1 (%) | 2 (%) | 3 (%) | 4 (%) |
|---|---|---|---|---|
| Protein*[1] | 23.05 | 28.65 | 28.45 | 30.05 |
| (Protein level) | (20) | (20) | (20) | (20) |
| Methionine*[2] | 0.1 | 0.1 | 0.1 | 0.1 |
| Lard | 5 | 5 | 5 | 5 |
| Corn oil | 1 | 1 | 1 | 1 |
| Mineral mixture*[3] (AIN-76) | 3.5 | 3.5 | 3.5 | 3.5 |
| Vitamin mixture (AIN-76) | 1 | 1 | 1 | 1 |
| Choline chloride | 0.2 | 0.2 | 0.2 | 0.2 |
| Cellulose | 5 | 5 | 5 | 5 |
| Sucrose | 60.4 | 54.8 | 55.0 | 53.4 |
| Cholesterol | 0.5 | 0.5 | 0.5 | 0.5 |
| Sodium cholate | 0.25 | 0.25 | 0.25 | 0.25 |

Notes)
*[1](Protein)
Group 1: Promic P (isolated soybean protein) (bound phospholipid content: 1%)
Group 2: Mixture of Promic P and SLP-White (soybean lecithin) obtained in Comparative Example 1 (bound phospholipid content: 0.8%, free phospholipid content: 20%)
Group 3: Protein/phospholipid complex obtained in Example 3 (Promic P/SLP-White complex) (bound phospholipid content: 20%, free phospholipid content: 1.0%)
Group 4: Protein/enzyme-modified phospholipid complex obtained in Example 2 (Promic P/Elmizer AC complex) (bound phospholipid content: 20%, free phospholipid content: 1.0%)
*[2]Methionine, an essential amino acid, was added in order to make the nutritive values of all the compositions equal.
*[3]American Institute of Nutrition [J. of Nutrition, 107, 1340 (1977)]

The results are shown in Table 2.

TABLE 2

| Test Group | Total Cholesterol Conc. in Serum (mg/dl) | HDL Cholesterol Conc. in Serum (mg/dl) | Arterio-sclerosis Index* | Total Cholesterol Conc. in Liver (mg/g of liver) |
|---|---|---|---|---|
| 1 | 111.0 ± 10.0 | 14.3 ± 1.0 | 0.14 ± 0.01 | 25.1 ± 1.3 |
| 2 | 80.8 ± 6.4 | 20.0 ± 0.9 | 0.25 ± 0.02 | 22.3 ± 1.0 |
| 3 | 79.3 ± 7.1 | 25.5 ± 1.7 | 0.33 ± 0.02 | 19.2 ± 1.2 |
| 4 | 77.2 ± 4.5 | 26.2 ± 1.0 | 0.35 ± 0.02 | 16.3 ± 1.3 |

(Numerical value: mean ± standard error)
Note)
*The arteriosclerosis index shows the value of (HDL cholesterol conc. in serum)/(total cholesterol conc. in serum).

As shown in the above table, Test Groups 3 and 4 were almost equal to Test Group 2 in total cholesterol concentration in serum, but showed higher HDL cholesterol concentration in serum as compared with Test Groups 1 and 2. The relationship between the total cholesterol concentration in serum and the HDL cholesterol concentration in serum was expressed as the arteriosclerosis index. Test Groups 3 and 4 showed higher arteriosclerosis index as compared with Test Groups 1 and 2, which indicates that the cholesterol metabolism in serum was improved in Test Groups 3 and 4. Test groups 3 and 4 also showed lower total cholesterol concentration in liver as compared with Test Groups 1 and 2. No significant difference was observed in feed intake or increase in body weight between the test groups.

TEST EXAMPLE 2

The test was carried out in the same manner as in Test Example 1, except that the feed compositions shown in Table 3 were used. The results are shown in Table 4.

TABLE 3

| Ingredient | Test Group 5 (%) | 6 (%) |
|---|---|---|
| Protein*[1] | 34.35 | 32.65 |
| (Protein) | (20) | (20) |
| Lard | 5 | 5 |
| Corn oil | 1 | 1 |
| Mineral mixture (AIN-76) | 3.5 | 3.5 |
| Vitamin mixture (AIN-76) | 1 | 1 |
| Choline chloride | 0.2 | 0.2 |
| Cellulose | 5 | 5 |
| Sucrose | 49.2 | 50.9 |
| Cholesterol | 0.5 | 0.5 |
| Sodium cholate | 0.25 | 0.25 |

Note)
*[1](Protein)
Group 5: Mixture of Promic P hydrolyzate and SLP-White obtained in Comparative Example 3 (bound phospholipid content: 0.8%, free phospholipid content: 20%)
Group 6: Protein hydrolyzate/phospholipid complex obtained in Example 9 (Promic P hydrolyzate/SLP-White complex) (bound phospholipid content: 20%, free phospholipid content: 1.0%)

TABLE 4

| Test Group | Total Cholesterol Conc. in Serum (mg/dl) | HDL Cholesterol Conc. in Serum (mg/dl) | Arterio-sclerosis Index | Total Cholesterol Conc. in Liver (mg/g of liver) |
|---|---|---|---|---|
| 5 | 72.7 ± 3.1 | 35.2 ± 1.3 | 0.49 ± 0.03 | 7.4 ± 0.7 |
| 6 | 68.3 ± 3.6 | 32.0 ± 2.3 | 0.49 ± 0.03 | 4.7 ± 0.4 |

(Numerical value: mean ± standard error)

As shown in the above table, Test Group 6 was equal to Test Group 5 in arteriosclerosis index, but showed lower total cholesterol concentration in liver. No significant difference was observed in feed intake or increase in body weight between the test groups.

TEST EXAMPLE 3

The test was carried out in the same manner as in Test Example 1, except that the feed compositions shown in Table 5 were used. The results are shown in Table 6.

TABLE 5

| Ingredient | Test Group 7 (%) | 8 (%) | 9 (%) |
|---|---|---|---|
| Protein*[1] | 23.05 | 32.3 | 34.8 |
| (Protein level) | (20) | (20) | (20) |
| Methionine | 0.1 | 0.04 | 0.04 |
| Tryptophan | 0 | 0.01 | 0.01 |
| Lard | 5 | 5 | 5 |
| Corn oil | 1 | 1 | 1 |
| Mineral mixture (AIN-76) | 3.5 | 3.5 | 3.5 |
| Vitamin mixture (AIN-76) | 1 | 1 | 1 |
| Choline chloride | 0.2 | 0.2 | 0.2 |
| Cellulose | 5 | 5 | 5 |

TABLE 5-continued

|  | Test Group | | |
|---|---|---|---|
| Ingredient | 7 (%) | 8 (%) | 9 (%) |
| Sucrose | 60.4 | 51.2 | 48.7 |
| Cholesterol | 0.5 | 0.5 | 0.5 |
| Sodium cholate | 0.25 | 0.25 | 0.25 |

Note)
*[1](Protein)
Group 7: Promic P (bound phospholipid content: 1%)
Group 8: Hydrolyzate of soybean protein/enzyme-modified lecithin complex (Promic P/Elmizer AC complex) obtained in Example 5 (bound phospholipid content: 20%, free phospholipid content: 0.5%)
Group 9: Soybean protein hydrolyzate/enzyme-modified lecithin complex obtained in Example 8 (Promic P hydrolyzate/Elmizer AC complex) (bound phospholipid content: 20%, free phospholipid content: 1.0%)

TABLE 6

| Test Group | Total Cholesterol Conc. in Serum (mg/dl) | HDL Cholesterol Conc. in Serum (mg/dl) | Arterio-sclerosis Index | Total Cholesterol Conc. in Liver (mg/g of liver) |
|---|---|---|---|---|
| 7 | 103.8 ± 9.7 | 34.7 ± 2.5 | 0.35 ± 0.04 | 28.7 ± 1.5 |
| 8 | 75.4 ± 5.3 | 53.4 ± 3.1 | 0.71 ± 0.02 | 4.3 ± 0.3 |
| 9 | 81.4 ± 4.7 | 53.5 ± 2.7 | 0.73 ± 0.02 | 5.3 ± 0.3 |

(Numerical value: mean ± standard error)

As shown in the above table, the arteriosclerosis indices of Test Groups 8 and 9 were higher than that of Test Group 7, which indicates that the cholesterol metabolism in serum was improved in Test Groups 8 and 9. In addition, Test Groups 8 and 9 showed total cholesterol concentration in liver much lower than that of Test Group 7; the total cholesterol concentration in liver of Test Group 8 was lower than that of Test Group 9. No significant difference was observed in feed intake or increase in body weight between the test groups.

TEST EXAMPLE 4

The test was carried out in the same manner as in Test Example 1, except that the feed compositions shown in Table 7 were used. The results are shown in Table 8.

TABLE 7

|  | Test Group | | | | |
|---|---|---|---|---|---|
| Ingredient | 10 (%) | 11 (%) | 12 (%) | 13 (%) | 14 (%) |
| Protein*[1] | 27.59 | 28.69 | 28.69 | 37.15 | 40.65 |
| (Protein level) | (20) | (20) | (20) | (20) | (20) |
| Tryptophan | 0.04 | 0.04 | 0.04 | 0.02 | 0.02 |
| Lysine | 0.82 | 0.82 | 0.82 | 0.72 | 0.72 |
| Threonine | 0.2 | 0.2 | 0.2 | 0.16 | 0.16 |
| Lard | 5 | 5 | 5 | 5 | 5 |
| Corn oil | 1 | 1 | 1 | 1 | 1 |
| Mineral mixture*[3] (AIN-76) | 3.5 | 3.5 | 3.5 | 3.5 | 3.5 |
| Vitamin mixture (AIN-76) | 1 | 1 | 1 | 1 | 1 |
| Choline chloride | 0.2 | 0.2 | 0.2 | 0.2 | 0.2 |
| Cellulose | 5 | 5 | 5 | 5 | 5 |
| Sucrose | 54.9 | 53.8 | 53.8 | 45.5 | 42.0 |
| Cholesterol | 0.5 | 0.5 | 0.5 | 0.5 | 0.5 |
| Sodium cholate | 0.25 | 0.25 | 0.25 | 0.25 | 0.25 |

Note)
*[1](Protein)
Group 10: Wheat gluten (bound phospholipid content: 0.3%)
Group 11: Mixture of wheat gluten and enzyme-modified lecithin obtained in Comparative Example 2 (bound phospholipid content: 0.3%, free phospholipid content: 10%)
Group 12: Wheat gluten/enzyme-modified lecithin complex obtained in Example 1 (bound phospholipid content: 10%, free phospholipid content: 1.0%)
Group 13: Hydrolyzate of wheat gluten/enzyme-modified lecithin complex obtained in Example 4 (bound phospholipid content: 10%, free phospholipid content: 0.3%)
Group 14: Wheat gluten hydrolyzate/enzyme-modified lecithin complex obtained in Example 7 (bound phospholipid content: 10%, free phospholipid content: 1.0%)

TABLE 8

| Test Group | Total Cholesterol Conc. in Serum (mg/dl) | HDL Cholesterol Conc. in Serum (mg/dl) | Arterio-sclerosis Index | Total Cholesterol Conc. in Liver (mg/g of liver) |
|---|---|---|---|---|
| 10 | 132.5 ± 7.4 | 16.7 ± 1.4 | 0.13 ± 0.02 | 22.8 ± 1.0 |
| 11 | 113.7 ± 10.3 | 15.8 ± 1.2 | 0.14 ± 0.01 | 26.5 ± 2.5 |
| 12 | 83.5 ± 6.9 | 21.5 ± 1.8 | 0.27 ± 0.03 | 19.9 ± 1.3 |
| 13 | 62.2 ± 5.6 | 34.8 ± 1.8 | 0.58 ± 0.04 | 7.3 ± 0.4 |
| 14 | 79.6 ± 6.7 | 28.7 ± 2.4 | 0.37 ± 0.03 | 18.9 ± 1.5 |

(Numerical value: mean ± standard error)

As shown in the above table, the arteriosclerosis indices of Test Groups 12-14 were higher than those of Test Groups 10 and 11, which indicates that the cholesterol metabolism in serum was improved in Test Groups 12-14. In addition, Test Groups 12-14 showed lower total cholesterol concentration in liver as compared with Test Groups 10 and 11; in particular, the total cholesterol concentration in liver of Test Group 13 was much the lowest. No significant difference was observed in feed intake or increase in body weight between the test groups.

Certain embodiments of the invention are illustrated in the following Examples and Comparative Examples.

BEST MODE FOR CARRYING OUT THE INVENTION

Example 1

To 1 kg of Regular Gluten A (wheat gluten, Bunge, bound phospholipid content: 0.3%) was added 2.4 l of a 5% solution prepared by dispersing Elmizer AC (enzyme-modified lecithin, Kyowa Hakko Kogyo Co., Ltd.) in water. The mixture was kneaded by using a baker's mixer (100 r.p.m.) at room temperature for 10 minutes. The resulting reaction mixture was freeze-dried and then pulverized to obtain about 1.1 kg of a protein/phospholipid complex (bound phospholipid content: 10%, free phospholipid content: 1.0%).

Example 2

To 1 kg of Promic P (isolated soybean protein, Kyowa Hakko Kogyo Co., Ltd., bound phospholipid content: 1.0%) was added 10 L of a 2.5% solution prepared by dispersing Elmizer AC in water. The mixture was stirred rapidly (10,000 r.p.m.) at room temperature for 10 minutes. The resulting reaction mixture was freeze-dried and then pulverized to obtain 1.1 kg of a protein/phospholipid complex (bound phospholipid content: 20%, free phospholipid content: 1.0%).

Example 3

The same procedure as in Example 2 was repeated, except that SLP-White (purified soybean lecithin, True Lecithin mfg. Co., Ltd.) was used in place of Elmizer AC, whereby about 1.1 kg of a protein/phospholipid complex (bound phospholipid content: 20%, free phospholipid content: 1.0%) was obtained.

Example 4

The protein/phospholipid complex obtained in Example 1 (1 kg) was dispersed in 9 L of water, followed by addition of 2 N hydrochloric acid to adjust the solution to pH 2. To the resulting solution was added pepsin [activity; 1:10,000 (this means that 1 g of the pepsin is capable of hydrolyzing 10,000 g of egg white protein at 50° C. in 2 hours under acidic conditions with hydrochloric acid), Nacalai Tesque, Inc.] in an amount of 1% based on the protein/phospholipid complex. The mixture was allowed to stand at 37° C. for 24 hours, followed by heating at 90° C. for one hour to stop the reaction. The reaction mixture was neutralized with 2 N sodium hydroxide, and then centrifuged. To the obtained precipitate was added water, and the mixture was centrifuged again. This procedure was repeated twice, whereby the precipitate was washed. The precipitate was freeze-dried and then pulverized to obtain 200 g of a hydrolyzate of the protein/phospholipid complex which is slightly soluble in water (molecular weight: ca. 15,000, bound phospholipid content: 10%, free phospholipid content: 0.3%). The molecular weight was determined by sodium dodecyl sulfate (SDS)-polyacrylamide gel electrophoresis (the same method was employed for the determination of molecular weight in the following Examples).

Example 5

The same procedure as in Example 4 was repeated, except that the protein/phospholipid complex obtained in Example 2 was used in place of the protein/phospholipid complex obtained in Example 1, whereby 200 g of a hydrolyzate of the protein/phospholipid complex which is slightly soluble in water (molecular weight: ca. 15,000, bound phospholipid content: 20%, free phospholipid content: 0.5%) was obtained.

The nitrogen contents of the protein used as the starting material and the protein contained in the obtained hydrolyzate of the protein/phospholipid complex were respectively determined by the Kjeldahl method. Multiplication of the obtained values by a conversion factor of 6.25 gave the weights of the proteins, and the protein recovery calculated as the ratio of the amount of the protein contained in the hydrolyzate to that of the protein used as the starting material was 19.1%.

Example 6

The same procedure as in Example 4 was repeated, except that the protein/phospholipid complex obtained in Example 3 was used in place of the protein/phospholipid complex obtained in Example 1, whereby 200 g of a hydrolyzate of the protein/phospholipid complex which is slightly soluble in water (molecular weight: ca. 15,000, bound phospholipid content: 20%, free phospholipid content: 0.5%) was obtained.

Example 7

Regular Gluten A (bound phospholipid content: 0.3%) (1 kg) was dispersed in 9 l of water, followed by addition of 2 N hydrochloric acid to adjust the solution to pH 2. To the resulting solution was added pepsin (activity; 1:10,000, Nacalai Tesque, Inc.) in an amount of 1% based on Regular Gluten A. The mixture was allowed to stand at 37° C. for 24 hours, followed by heating at 90° C. for one hour to stop the reaction. The reaction mixture was neutralized with 2 N sodium hydroxide, and then centrifuged. To the obtained precipitate was added water, and the mixture was centrifuged again. This procedure was repeated twice, whereby the precipitate was washed. The precipitate was freeze-dried and then pulverized to obtain 200 g of a protein hydrolyzate (molecular weight: ca. 15,000). To 200 g of the obtained protein hydrolyzate was added 1.0 l of a 2.5% solution prepared by dispersing Elmizer AC in water, and the mixture was stirred rapidly (10,000 r.p.m.). The resulting reaction mixture was freeze-dried and then pulverized to obtain 220 g of a protein hydrolyzate/phospholipid complex (bound phospholipid content: 10%, free phospholipid content: 1.0%).

Example 8

Promic P (bound phospholipid content: 1.0%) (1 kg) was dispersed in 9 l of water, followed by addition of 2 N hydrochloric acid to adjust the solution to pH 2. To the resulting solution was added pepsin (activity; 1:10,000, Nacalai Tesque, Inc.) in an amount of 1% based on Promic P. The mixture was allowed to stand at 37° C. for 24 hours, followed by heating at 90° C. for one hour to stop the reaction. The reaction mixture was neutralized with 2 N sodium hydroxide, and then centrifuged. To the obtained precipitate was added water, and the mixture was centrifuged again. This procedure was repeated twice, whereby the precipitate was washed. The precipitate was freeze-dried and then pulverized to obtain 200 g of a protein hydrolyzate (molecular weight: ca. 15,000). To 200 g of the obtained protein hydrolyzate was added 2.0 l of a 2.5% solution prepared by dispersing Elmizer AC in water, and the mixture was stirred rapidly (10,000 r.p.m.). The resulting reaction mixture was freeze-dried and then pulverized to obtain 250 g of a protein hydrolyzate/phospholipid complex (bound phospholipid content: 20%, free phospholipid content: 1.0%).

The protein recovery calculated as the ratio of the amount of the protein contained in the obtained protein hydrolyzate/phospholipid complex to that of the protein used as the starting material in the same manner as in Example 5 was 12.4%.

Example 9

The same procedure as in Example 8 was repeated, except that SLP-White was used in place of Elmizer AC, whereby 250 g of a protein hydrolyzate/phospholipid complex (bound phospholipid content: 20%, free phospholipid content: 1.0%) was obtained.

Comparative Example 1

Promic P (bound phospholipid content: 1.0%) (1 kg) was mixed with 250 g of SLP-White to obtain 1250 g of a protein/phospholipid mixture (bound phospholipid content: 0.8%, free phospholipid content: 20%).

Comparative Example 2

Regular Gluten A (bound phospholipid content: 0.3%) (1 kg) was mixed with 110 g of Elmizer AC to obtain 1110 g of a protein/enzyme-modified lecithin mixture (bound phospholipid content: 0.3%, free phospholipid content: 10%).

Comparative Example 3

Promic P (bound phospholipid content: 1%) (1 kg) was dispersed in 9 l of water, followed by addition of 2 N hydrochloric acid to adjust the solution to pH 2. To the resulting solution was added pepsin (activity; 1:10,000, Nacalai Tesque, Inc.) in an amount of 1% based on Promic P. The mixture was allowed to stand at 37° C. for 24 hours, followed by heating at 90° C. for one hour to stop the reaction. The reaction mixture was neutralized with 2 N sodium hydroxide, and then centrifuged. To the obtained precipitate was added water, and the mixture was centrifuged again. This procedure was repeated twice, whereby the precipitate was washed. The precipitate was freeze-dried and then pulverized to obtain 200 g of a protein hydrolyzate (molecular weight: ca. 15,000). The obtained protein hydrolyzate (1 kg) was mixed with 250 g of SLP-White to obtain 1250 g of a protein hydrolyzate/phospholipid mixture (bound phospholipid content: 0.8%, free phospholipid content: 20%).

Example 10

Hamburgers (two serving) are prepared from the Following ingredients

| | |
|---|---|
| Onion | Half |
| Minced meat | 100 g |
| Water | 29.2 g |
| Lard | 11.8 g |
| Slightly water-soluble product obtained in Example 5 | 9 g |
| Egg | One |
| Crumbs | Small quantity |
| Seasonings | Small quantity |

Example 11

Cookies (30 pieces) are prepared from the following ingredients.

| | |
|---|---|
| Soft flour | 100 g |
| Starch | 74 g |
| Water | 14 g |
| Slightly water-soluble product obtained in Example 5 | 9 g |
| Baking powder | 2 Tsp. |
| Salt | ½ Tsp. |
| Egg | One |
| Butter | 80 g |
| Milk | 2 Tbsp. |
| Honey | Small quantity |

Example 12

A powdery protein to be used in a liquid preparation is prepared from the following ingredients.

| | |
|---|---|
| Slightly water-soluble product obtained in Example 5 | 80 g |
| Casein sodium | 17.5 g |
| L-Valine | 0.5 g |
| Ferric pyrophosphate (iron source) | 0.1 g |
| Phoscal EFC (calcium source, Nikko Fine Products) | 1 g |
| Vitamin Mix (Merck & Co., Inc.) | 1 g |

A liquid preparation is prepared by dispersing 20 g of the powdery protein in 180 ml of water.

Example 13

Tablets are prepared from the following ingredients.

| | |
|---|---|
| Slightly water-soluble product obtained in Example 5 | 2 g |
| Powdery sugar | 2.6 g |
| Ascorbic acid | 150 mg |
| Citric acid | 0.1 g |
| Sucrose stearate | 150 mg |
| Flavor | 15 mg |

INDUSTRIAL APPLICABILITY

The present invention provides a lipid metabolism improving agent and a functional food.

What is claimed is:

1. A method for lowering serum cholesterol of an animal, which comprises administering to the animal a protein hydrolyzate/phospholipid complex, said complex containing at least 10 wt % of bound phospholipid, said bound phospholipid in the complex being a phospholipid which remains bound to the protein hydrolyzate after being treated with a nonpolar organic solvent, wherein said protein is soybean protein and said phospholipid is phospholipase A2-modified phospholipid.

2. A method for producing food or feed, which comprises adding, to a food or feed material, a protein hydrolyzate/phospholipid complex, said protein hydrolyzate/phospholipid complex containing at least 10 wt % of bound phospholipid, said bound phospholipid in the complex being a phospholipid which remains bound to the protein hydrolyzate after being treated with a nonpolar organic solvent, wherein said protein is soybean protein and said phospholipid is phospholipase A2-modified phospholipid.

3. The method according to claim 1, wherein the phospholipase A2-modified phospholipid is phospholipase A2-modified lecithin obtainable by treating lecithin with phospholipase A2.

4. The method according to claim 1, wherein the animal is human.

5. The method according to claim 2, wherein the phospholipase A2-modified phospholipid is phospholipase A2-modified lecithin obtainable by treating lecithin with phospholipase A2.

6. The method according to claim 1, wherein said complex contains 10-50 wt % of the bound phospholipid.

7. The method according to claim 6, wherein said complex contains 20-50 wt % of the bound phospholipid.

8. The method according to claim 2, wherein said complex contains 10-50 wt % of the bound phospholipid.

9. The method according to claim 8, wherein said complex contains 20-50 wt % of the bound phospholipid.

* * * * *